United States Patent [19]

Burkholder

[11] 4,420,376

[45] Dec. 13, 1983

[54] SEPARATION OF RESORCINOL FROM NON-EXTRACTABLE IMPURITIES

[75] Inventor: Ward J. Burkholder, Gonzales, La.

[73] Assignee: The Goodyear Tire & Rubber Company, Akron, Ohio

[21] Appl. No.: 410,346

[22] Filed: Aug. 23, 1982

[51] Int. Cl.$^3$ .................. B01D 3/38; B01D 3/40; C07C 39/08

[52] U.S. Cl. .................. 203/29; 203/28; 203/39; 203/43; 203/48; 203/69; 203/85; 203/96; 568/753; 568/763

[58] Field of Search .................. 203/28, 29, 33, 36, 203/37, 95, 96, 69, 85, 39, 43, 48; 568/753, 763

[56] References Cited

U.S. PATENT DOCUMENTS

| | | | |
|---|---|---|---|
| 2,736,753 | 2/1956 | Jacobs | 203/69 |
| 2,789,142 | 4/1957 | Graham | 568/753 |
| 3,509,028 | 4/1970 | Budd et al. | 203/69 |
| 4,192,958 | 3/1980 | Hashimoto et al. | 568/763 |
| 4,273,623 | 6/1981 | Hashimoto et al. | 203/95 |

FOREIGN PATENT DOCUMENTS

| | | | |
|---|---|---|---|
| 53-626 | 5/1978 | Japan | 568/763 |
| 873676 | 7/1961 | United Kingdom | 568/753 |

*Primary Examiner*—Wilbur L. Bascomb, Jr.
*Attorney, Agent, or Firm*—C. James Bushman; Alvin T. Rockhill

[57] ABSTRACT

An improved process for recovering high purity resorcinol produced by the rearrangement of m-diisopropylbenzene dihydroperoxide in which the rearranged product mixture is neutralized, the neutralized mixture being filtered, the filtrate being admixed with toluene, the acetone being removed by distillation and the acetone-free rearranged product/toluene mixture being steam distilled to provide an aqueous resorcinol containing phase from which the resorcinol is recovered.

7 Claims, No Drawings

4,420,376

SEPARATION OF RESORCINOL FROM NON-EXTRACTABLE IMPURITIES

BACKGROUND OF THE INVENTION

The present invention relates to an improvement in the oxidation-cleavage processs for preparing resorcinol from m-dialkylbenzene such as m-diisopropylbenzene (m-DIPB). The basic steps of the process and the reactions which occur throughout the process are given in the following prior art references: Britton et al, U.S. Pat. No. 1,934,656; Palfreeman et al, U.S. Pat. No. 2,130,151; Rodgers, U.S. Pat. No. 2,748,172; Great Britain Pat. No. 723,454; Great Britain Pat. No. 724,224; Great Britain Pat. No. 805,048; Great Britain Pat. No. 910,735; Japanese Pat. No. 172,351; and the paper by A. R. Graham (The Distillers Chemicals and Plastics Ltd. Great Britain) entitled "The Production of Resorcinol by the Oxidation of m-Diisopropylbenzene," presented at the Seventh International Meet, World Petroleum Congress, April, 1967.

In the first stage of the process, m-DIPB is oxidized to a mixture of m-diisopropylbenzene monohydroperoxide, m-diisopropylbenzene dihydroperoxide, and other by-products. The second stage of the process consists of extracting and separating the dihydroperoxide and certain impurities from the monohydroperoxide and other impurities. The monohydroperoxide-containing phase is then treated and re-cycled to the oxidizer. The dihydroperoxide-containing phase is treated and subjected to acid catalyzed rearrangement or cleavage in a substantially anhydrous organic solvent consisting of acetone or mixtures of acetone and methyl isobutyl ketone (MIBK). Small quantities of strong acids, normally sulphuric acid, are used as the catalyst. It is important to choose conditions for carrying out the cleavage at high rates and low acid concentrations to minimize loss of yield by the further reaction of resorcinol and acetone to form resins, a process which is also acid catalyzed.

Since the m-diisopropylbenzene dihydroperoxide contains m-diisopropylbenzene hydroxyhydroperoxide as an impurity, the acid catalyzed change results in a mixture comprising acetone, MIBK if used, resorcinol, m-isopropylolphenol (from the m-diisopropylbenzene hydroxyhydroperoxide), and other impurities.

The next stage of the process consists of separating and removing the resorcinol as a high purity product. This is accomplished by neutralizing the rearranged product mixture, removing the volatile solvent and thereafter separating the resorcinol from the impurities.

Thus, in the article by A. R. Graham cited previously, the cleavage product was neutralized to a pH of 3.5–4.0 and steam distilled to remove the volatile solvent. The kettle temperature was then raised, and at temperatures between 200° C. and 300° C., resorcinol and by-product phenols were steam distilled and adducts were cracked. Resorcinol-isopropenylphenol adducts were cracked in superheated steam at about 250° C. The distillate was collected in a mixture of toluene and water. The resorcinol dissolved in the aqueous phase from which it was isolated by azeotropic dehydration with toluene and crystallization from the toluene solution. The by-products m-isopropylphenol and m-isopropenylphenol and dimers of the latter dissolved in the toluene phase. This process results in a resorcinol product which is impure due to the presence of the impurity m-isopropylolphenol. The m-isopropylolphenol, which is present as an impurity in the rearranged cleavage product, is volatile to nearly the same extent as resorcinol and is water soluble. This, it is distilled along with the resorcinol and accumulates in the aqueous phase with the resorcinol.

Other potential methods of recovering a good yield of resorcinol of satisfactory purity include fractional distillation under vacuum; however, this process causes decomposition of the m-isopropyolphenol to m-isopropenylphenol and water. The water forms azeotropes and/or causes, in effect, a steam distillation. In either case, the distillation equilibrium is upset, the desired separation is not achieved, and the overhead product is water wet. In addition, there is, at times, an exothermic reaction which is believed to result from the polymerization of the m-isopropenylphenol, or its alkylation reactions with resorcinol, itself or other impurities.

Treatment of the volatile solvent-free rearranged cleavage product with a liquid which is a solvent for the majority of the impurities and a poor solvent for resorcinol, such as toluene, also does not remove the m-isopropylolphenol since the solubility of the latter and resorcinol are similar.

Thus, there is a need to improve the oxidation-cleavage process for preparing resorcinol from m-dialkylbenzene such that the resorcinol obtained is free from any m-hydroxyalkyl phenol, e.g. m-isopropylolphenol.

SUMMARY OF THE INVENTION

I have now found that m-isopropylolphenol can be dehydrated under steam stripping conditions to m-isopropenylphenol. Thus, the presence of a refluxing liquid in the volatile solvent-free rearranged cleavage product during steam stripping of the latter minimizes or prevents carryover of the m-isopropylolphenol and certain heavier by-products into the distillate with the resorcinol, and increases the residence time of the m-isopropylolphenol in the steam stripper thus enhancing its decomposition to m-isopropenylphenol.

It is therefore an object of this invention to provide a process for separating non-extractable impurities from resorcinol obtained by the oxidation of a m-dialkylbenzene such as m-DIPB.

It is another object of this invention to reduce the concentration of m-isopropylolphenol in resorcinol obtained by the oxidation of m-DIPB.

It is still another object of this invention to provide an improved process for the manufacture of high quality resorcinol by oxidizing m-DIPB and rearranging the m-dihydroperoxide so obtained.

These and other objects of this invention will become apparent to one skilled in the art upon reading the specification and the appended claims.

In accordance with this invention, a process has been developed for recovery of high purity resorcinol from the neutralized rearranged product solution. The process consists of: adding toluene to the neutralized, filtered rearranger effluent; distilling the acetone from the mixture; steam distilling the resorcinol from materials boiling higher than resorcinol while simultaneously cracking some of the heavier materials to liberate resorcinol and dehydrating m-isopropyolphenol to m-isopropenylphenol; separating the aqueous condensate from the toluene layer; and thereafter recovering the purified resorcinol from the aqueous phase by known means, such as by extraction, distillation, fractionation or crystallization.

DESCRIPTION OF THE PREFERRED EMBODIMENTS

The rearranged product solution resulting from the acid catalyzed rearrangement of m-diisopropylbenzene dihydroperoxide (m-DIX) must first be neutralized since the acid catalyzes alkylation and condensation reactions such as between resorcinol, m-isopropenylphenol, m-isopropylolphenol, acetone, and the like. However, it is known that aqueous solutions of ammonium salts containing ammonia or amines cause ammonolysis of resorcinol to form m-aminophenol or its derivatives. Thus, it is preferred that the rearranged product solution be neutralized with ammonia to a pH in the range of from about 4.5 to about 6.3, measured as a 10% solution of rearranged product solution in acetone, preferably from about 5.0 to about 6.3.

The neutralized rearranged product solution must be filtered to remove the ammonium salts developed as a result of the neutralization.

The neutralized, filtered rearranged product solution containing resorcinol, acetone and impurities is mixed with toluene in a weight ratio of rearranged product solution to toluene of from about 4:1 to about 1:2, preferably from about 3:1 to about 1:1. The acetone is then distilled from the mixture at reflux temperatures in the range of from about 110° C. to about 118° C. It was determined that 114° C. is the temperature of a refluxing mixture of equal weights of toluene and resorcinol. Such a mixture consists of two liquid phases. The solubility of toluene in the resorcinol layer was found to be 25.8%. The solubility of resorcinol in toluene exceeds 10% at 114° C. Both the bottoms temperature and the resorcinol solubility will be affected by the dissolved impurities that are present with the toluene and resorcinol. The boiling point of toluene is the same as the melting point of resorcinol. Elevation of the boiling point of toluene by the dissolved resorcinol will ensure that the temperature is always above the resorcinol melting point.

The acetone-free rearranged product solution is then steam distilled to separate resorcinol from the heavier impurities, to crack some of the heavier impurities to liberate resorcinol therefrom, and to dehydrate m-isopropylolphenol to m-isopropenylphenol. The bottoms temperature (temperature of the liquid in the distillation container) should be in the range of from about 130° C. to about 300° C., preferably from about 150° C. to about 195° C. The toluene either hinders the m-isopropylolphenol from distilling or increases the residence time of the m-isopropylolphenol in the distillation container thus increasing the extent of dehydration of the m-isopropylolphenol to m-isopropenylphenol. The latter is easily separated from resorcinol by extraction.

The distillate separates into two phases, an aqueous phase containing the resorcinol and a toluene phase. The aqueous phase is separated from the toluene phase and thereafter extracted with toluene.

The resorcinol can be recovered from the aqueous phase in high purity by various means such as by distillation of the majority of the water, azeotropic distillation of the remainder of the water with toluene, and crystallization.

The following non-limiting examples will illustrate the preferred embodiments of the inventive process of this invention.

EXAMPLE 1

An acetone solution containing 13.32% of m-DIX was batch rearranged using 0.6% $H_2SO_4$ at reflux temperature. The m-DIX addition time was 8.33 minutes. Then refluxing was continued for five minutes. Thereafter, the solution was cooled to ambient temperature, neutralized with $NH_3$ to a pH of 4.8 (as measured in a 10% solution in acetone), filtered, and the pH readjusted to 4.8 with $NH_3$. The resorcinol yield was 71.6%.

The acetone was removed by batch distillation of a mixture of equal parts of toluene and the rearranged product solution through a short packed column without reflux until the overhead temperature reached 110° C. The total distillation time was 17 minutes. No resorcinol was detectable in the distillate. Some toluene distilled with the acetone, so the residue was readjusted to the original weight of product solution by adding make-up toluene. The acetone content was 0.06%; i.e. 99.93% of the original acetone was removed. The analyses of the original and final solutions for resorcinol (by iodometric titration) indicated "176%" recovery of the resorcinol.

An aliquot of the rearranged product/toluene mixture was steam distilled for one hour at a flask temperature of 127°–153° C. and an overhead temperature of 110°–137° C. The steam distillation apparatus consisted of a pump to feed boiled, deionized water to a coiled tube in an electric furnace, where it was converted to superheated steam. The steam was injected through a dip tube, which extended to the bottom of the distillation flask. Heat was applied to the flask by an electric mantle. The vapors from the flask passed upward through a short tube packed with Raschig rings and when to the condenser and separatory funnel, which served as a receiver/separator for the two condensed layer. Of the total resorcinol charged to the flask, 54.5% was found in the distillate. Water to toluene overhead was in a 7.5/1.0 ratio. Overall accountability was 88.8%. Of the resorcinol which went overhead, 98.6% was in the water layer. Resorcinol crystals, isolated after azeotropic distillation of the water, were 98.67% pure.

EXAMPLE 2

An aliquot of the rearranged product/toluene mixture of Example 1 was steam distilled for 1.25 hours at bottoms and overhead temperature ranges of 162°–174° C. and 136°–143° C., respectively. 80.2% of the resorcinol in the flask was distilled. Accountability of resorcinol was 83.7%. The resorcinol overhead, as a percentage of the total resorcinol found, was 95.7%, 99.3% of which was in the water layer.

Chromatographic separation of the toluene-extracted resorcinol indicated only a trace of m-isopropylolphenol present. The m-isopropylolphenol is not extractable with toluene from aqueous extracts of acetone-free rearranged product solution which has not been steam distilled. Thus, during the steam distillation of the acetone-free rearranged product solution containing toluene, either the m-isopropylolphenol does not distill or it is dehydrated to m-isopropenylphenol which is then extractable from resorcinol with toluene.

EXAMPLE 3

An acetone solution (containing 78% acetone) of m-DIX was rearranged at 70° C. and 5 minutes residence time in a continuous tubular rearranger using 0.2% H₂SO₄ as a catalyst. The m-DIX contained 78.94% m-DIX, 16.55% m-MOXOL, 0.34% m-MOX, 0.05rearranged at 70° C. and 5 minutes residence time in a continuous tubular rearranger using 0.2% H₂SO₄ as a catalyst. The m-DIX contained 78.94% m-DIX, 16.55% m-MOXOL, 0.34% m-MOX, 0.05% water and 4.12% other impurities (by column chromatography). The rearrangement yield to resorcinol was an unexplainably low 38%. The rearranged product solution was neutralized with ammonia to a pH of 2.75 (10% solution in acetone). GLC analyses of the rearranged product solution, aftThe rearrangement yield to resorcinol was an unexplainably low 38%. The rearranged product solution was neutralized with ammonia to a pH of 2.75 (10% solution in acetone). GLC analyses of the rearranged product solution, after adjustment of the pH to 6.05 (10% solution in acetone) indicated the presence of 0.5% m-isopropyolphenol, based on the weight of resorcinol. Moreover, the concentration of all of the impurities exceeded the concentration of resorcinol and the components heavier than resorcinol exceeded the components lighter than resorcinol, excluding solvent.

The acetone was removed by batch distillation of a mixture of the rearranged product solution and toluene. The concentration of toluene added was such that the weight ratio of acetone-free rearranged product solution to toluene was 2 to 1. The hot residue appeared to be a homogeneous solution; however, upon cooling, an upper toluene layer separated from a resorcinol/tar/toluene layer. The weight ratio of the lower layer was 20.05 times that of the upper layer.

Proportionate amounts of the two layers were mixed and steam distilled with 6 grams per minute of steam for 1.25 hours at 200°–239° C. flask temperature and 111°–144° C. overhead temperature. The ratio of the water layer to the toluene layer in the distillate was 20.1/1.0 (i.e. 4.75% of the distillate was toluene layer). 99.2% of the resorcinol distilled was in the toluene layer phase. Accountability of resorcinol was 185.8%; recovery of resorcinol in the distillate water phase was 169.2%. This can be explained by the cracking of materials heavier than resorcinol to liberate resorcinol. The resorcinol recovery based upon the m-DIX rearranged was about 55%. The recovery would be expected to be higher with higher rearrangement yields.

The foregoing disclosure and description of the invention is illustrative and explanatory thereof, and various changes in the method steps may be made within the scope of the appended claims without departing from the spirit of the invention.

I claim:

1. In a process for the manufacture of resorcinol from a rearranged oxidation product of m-diisopropylbenzene in an acetone solution, the improvement which comprises neutralizing said rearranged product to a pH, measured as 10% by weight solution in acetone of the rearranged oxidation product, in the range of from about 4.5 to about 6.3, filtering said neutralized solution to remove any salts therefrom, adding toluene to said filtered solution in an amount to provide a weight ratio of said filtered solution to toluene of from about 4:1 to about 1:2, distilling said acetone from the mixture of filtered solution and toluene at reflux temperature, steam distilling said acetone-free rearranged product-/toluene mixture at a bottoms temperature in the range of from about 130° C. to about 300° C., separating the aqueous resorcinol-containing phase from the toluene phase, and thereafter recovering the resorcinol from said aqueous phase.

2. The process of claim 1 wherein said pH is in the range from about 5.0 to about 6.3.

3. The process of claim 1 wherein said bottoms temperature is in the range from about 150° C. to about 195° C.

4. The process of claim 1, 2, or 3, wherein said weight ratio of said filtered solution to said toluene is from about 3:1 to about 1:1.

5. The process of claim 1, 2, or 3, wherein said reflux temperature is about 114° C.

6. The process of claim 1, 2, or 3, wherein said weight ratio of said filtered solution to said toluene is from about 3:1 to about 1:1, and wherein said reflux temperature is about 114° C.

7. The process of claim 1 wherein the rearranged product solution is neutralized with ammonia.

* * * * *

UNITED STATES PATENT OFFICE
CERTIFICATE OF CORRECTION

PATENT NO. : 4,420,376
DATED : December 13, 1983
INVENTOR(S) : Ward J. Burkholder It is certified that error appears in the above-identified patent and that said Letters Patent are hereby corrected as shown below:

Column 4, line 37, delete the word --layer-- and substitute therefor "layers".

Column 5, lines 3-6, delete the following: --0.05 rearranged at 70°C. and 5 minutes residence time in a continuous tubular rearranger using 0.2% $H_2SO_4$ as a catalyst. The m-DIX contained 78.94% m-DIX, 16.55% m-MOXOL, 0.34% m-MOX,--

Column 5, lines 12-16, delete the following: --product solution, afThe rearrangement yield to resorcinol was an unexplainably low 38%. The rearranged product solution was neutralized with ammonia to a pH of 2.75 (10% solution in acetone). GLC analyses of the rearranged--

Column 5, line 38, delete --toluene layer-- and insert therefor "water"

Signed and Sealed this

Twenty-ninth Day of May 1984

[SEAL]

Attest:

GERALD J. MOSSINGHOFF

Attesting Officer

Commissioner of Patents and Trademarks